United States Patent
Feng

[19]

[11] Patent Number: 6,162,215
[45] Date of Patent: Dec. 19, 2000

[54] CAUTERIZATION TREATMENT BY INFRARED RAYS

[76] Inventor: Yuan Feng Feng, No. 197, Sec. 2, Jungchinq Rd., Dayard, Taichung County, Taiwan

[21] Appl. No.: 09/219,188

[22] Filed: Dec. 23, 1998

[51] Int. Cl.⁷ ................................................. A61B 18/04
[52] U.S. Cl. ................................. 606/31; 606/9; 606/10
[58] Field of Search .................... 606/9, 10, 11, 606/13, 27, 28, 29, 30, 31; 607/96, 98, 99

[56] References Cited

U.S. PATENT DOCUMENTS

| | | | |
|---|---|---|---|
| 5,662,644 | 9/1997 | Swor | 606/9 |
| 5,814,040 | 9/1998 | Nelson et al. | 606/9 |

*Primary Examiner*—Linda C. M. Dvorak
*Assistant Examiner*—R. Kearney
*Attorney, Agent, or Firm*—Pro-Techtor International Services

[57] ABSTRACT

An infrared rays cauterizing structure is composed of a base, locating devices, fixed cauterizers and a hand-held cauterizer. In light of locating devices, the cauterizers can be located in proximity of a specific point of the human body without attendance of a medical personnel. The base is provided in the interior thereof with a plurality of temperature controllers and timers for regulating the treatment temperature and the treatment duration of a heater of the cauterizers. The heater is capable of bringing about a predetermined energy for treating disease or relieving pain of the specific point of the body of a patient under treatment.

2 Claims, 2 Drawing Sheets

CAUTERIZATION TREATMENT BY INFRARED RAYS

FIELD OF THE INVENTION

The present invention relates generally to a medical treatment, and more particularly to a cauterization treatment by infrared rays.

BACKGROUND OF THE INVENTION

The conventional cauterization treatment makes use of a hot medicine bar to treat disease or relieve pain of a specific point of human body. The treatment is carried out with hand holding the hot medicine bar for a predetermined period of time. As a result, a medical personnel doing the treatment can not do other chores at the time when the treatment is being carried out. In addition, the treatment can not be carried out simultaneously on several points of human body. In light of the temperature of the hot medicine bar being fixed at a high temperature, an over-treatment can result in the burn of the human body. Moreover, the hot medicine bar can not be held steadily with hand as long as the treatment lasts. To sum up, the conventional cauterization treatment is time-consuming and inefficient at best.

SUMMARY OF THE INVENTION

It is therefore the primary objective of the present invention to provide an infrared rays cauterizing structure which is composed of a base, a locating device, a fixed cauterizer and a hand-held cauterizer. The infrared rays cauterizing device is used for the "point" treatment of the human body without the prolonged attention of a medical personnel. The treatment temperature and the treatment duration are regulated by a temperature controller and a timer, which are mounted on the base.

It is another objective of the present invention to provide an infrared rays cuterizing structure which is composed of a heater, an infrared rays ceramic block, and a medicine plate. The heater is formed of a coil and provided in the center thereof with the infrared rays ceramic block which has a plurality of through holes. The medicine plate is disposed at the top of the heater and is formed of a predetermined drug. The operation of the heater is regulated by the temperature controller and the timer of the base. A predetermined energy is brought about by the infrared rays ceramic block in conjunction with the medicine plate.

DETAILED DESCRIPTION OF THE EMBODIMENT

Figure 2:
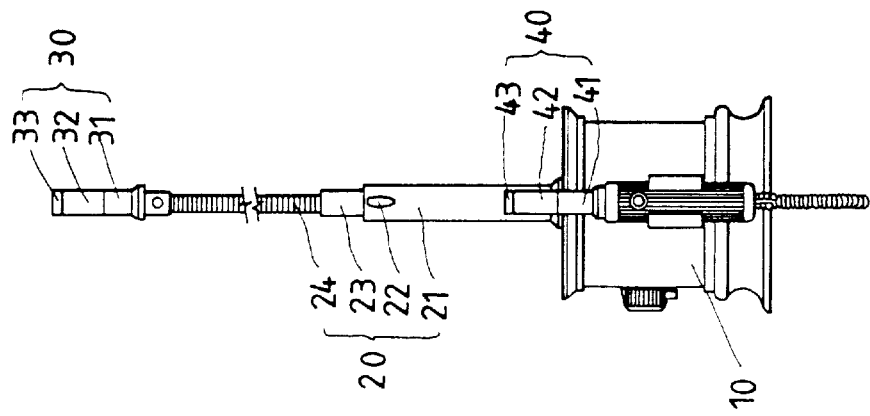
FIG. 2 shows a side schematic view of the preferred embodiment of the present invention.
Figure 1:
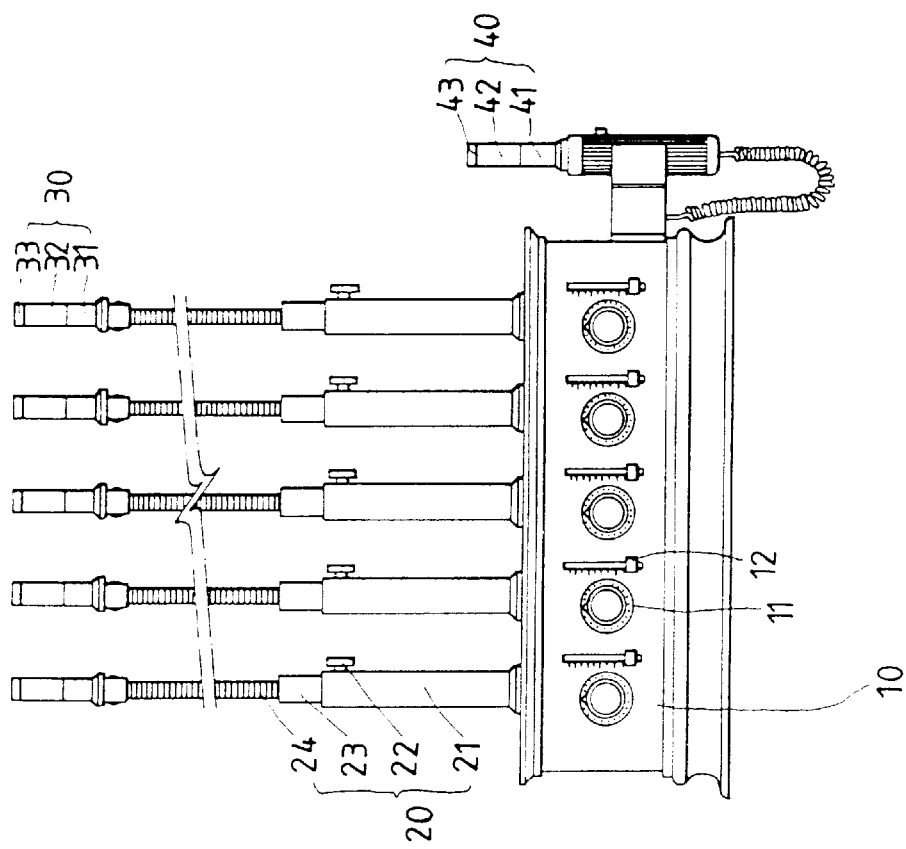
FIG. 1 shows a schematic view of the preferred embodiment of the present invention.
Figure 3:
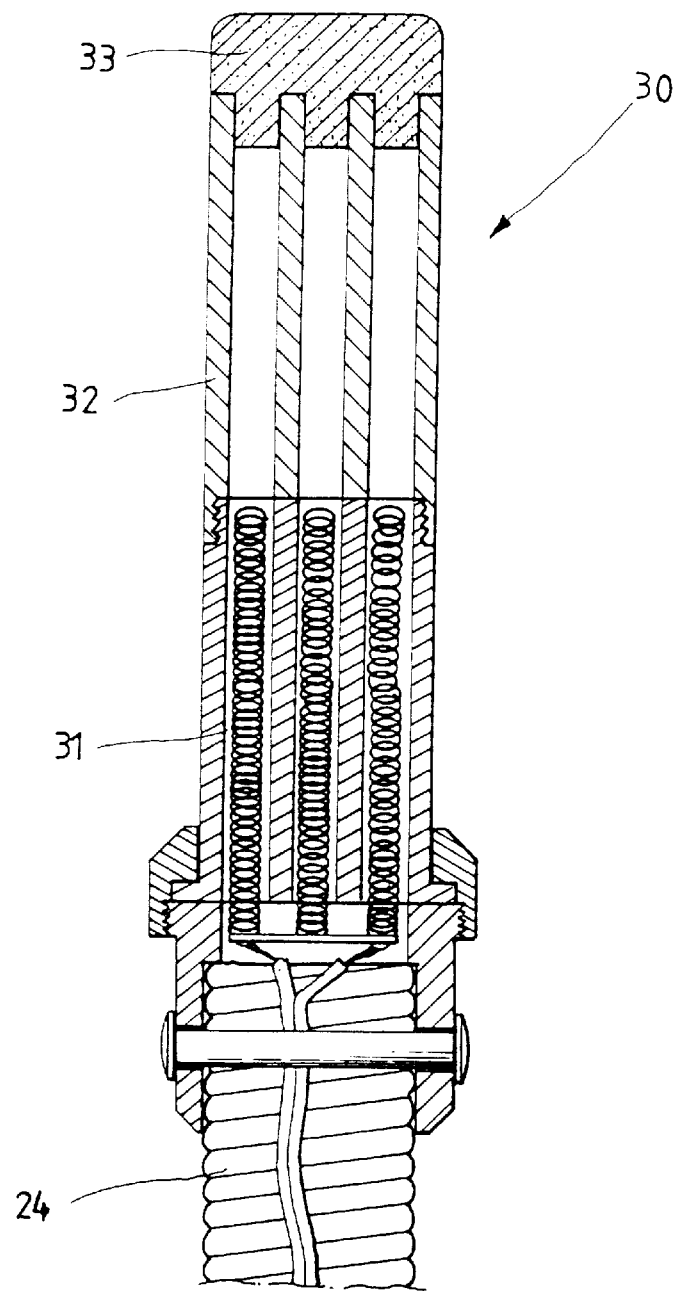
FIG. 3 shows a sectional view of the present invention.

As shown in FIGS. 1–3, an infrared rays cauterizing structure embodied in the present invention is composed of a base 10, a locating device, a fixed cauterizer 30, and a hand-held cauterizer 40.

The base 10 is provided in the interior thereof with a plurality of timers 11 and temperature controllers 12.

The locating device 20 consists of a locating tube 21, an expansion knob 22, an expansion tube 23, and a pliable tube 24. The locating tube 21 is of a hollow construction and is fastened at the top of the base 10. The expansion knob 22 is located in the proximity of the top end of the locating tube 21. One end of the expansion tube 23 is disposed in the locating tube 21. After the expansion tube 23 is expanded, it can be located by the expansion knob 22. The other end of the expansion tube 23 is provided with the pliable tube 24 which can be easily bent and located. The top of the base 10 may be also provided with a plurality of locating devices 20.

The fixed cauterizer 30 is fastened with other end of the pliable tube 24 and is composed of a heater 31, an infrared rays ceramic block 32, and a medicine plate 33. The base end of the fixed cauterizer 30 is in fact the heater 31 which is formed of coil. The infrared rays ceramic block 32 is located in the middle of the fixed cauterizer 30 and is provided with a plurality of through holes. The medicine plate 33 is disposed at the top end of the fixed cauterizer 30 and is made of a predetermined drug. The treatment temperature and the treatment duration of the heater 31 are regulated by the timers 11 and the temperature controllers 12.

The hand-held cauterizer 40 is composed of a heater 41, an infrared rays ceramic block 42, and a medicine plate 43. The hand-held cauterizer 40 is secured to one side of the base 10 by an elastic wire. The treatment temperature and the treatment duration of the heater 41 are regulated by the temperature controller 12 and the timer 11 of the base 10.

Prior to the use of the present invention in treating a patient, a specific point to be treated in the body of the patient must be determined. Thereafter, the present invention is located in the proximity of the specific point of the body of the patient by the expansion tube 23 and the pliable tube 24 of the locating device 20. The timer 11 and the temperature controller 12 of the base 10 are then so adjusted that the treatment duration and the treatment temperature of the heater 31 of the fixed cauterizer 30 are regulated, thereby resulting in the heating action on the infrared rays ceramic block 32 by the heater 31. The infrared rays emitted by the infrared rays ceramic block 32 are electromagnetic waves capable of a strong heating action and a strong permeability. As a result, the infrared rays can be used to destroy dead or unwanted tissue, prevent the spread of infection, seal the blood vessels, etc. In addition, the specific drug carried by the medicine plate 33 can be used via the ceramic block 32 to treat disease or relieve pain of a specific point of the body of a patient under treatment.

In light of the design of the locating device 20 of the present invention, the fixed cauterizer 30 can be located to bring about treatment without the attendance of a medical personnel. In addition, the present invention is provided with a plurality of the fixed cauterizers 30 to facilitate the treatment of various points of the body of a patient at the same time. The treatment temperature and the treatment duration are automatically regulated, thanks to the temperature controller 12 and the time 11 of the base 10.

The present invention is further provided with a hand-held cauterizer 40 which is intended for use in treating a hard-to-reach area of the human body.

The embodiment of the present invention described above is to be deemed in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. An infrared rays cauterizing structure comprising a base, a plurality of locating devices, and a plurality of cauterizers, said base provided in an interior thereof with a plurality of timers and temperature controllers, said locating devices being mounted on an upper surface of said base, said cauterizers being composed of a heater and other materials and disposed on other ends of said locating devices;

wherein said locating devices consist of a locating tube, an expansion tube, an expansion knob, and a pliable tube, said locating tube being fastened with a top of said base, said expansion tube having one end which is disposed in said locating tube such that said expansion tube can be regulated by said expansion knob, and that said expansion tube can be extracted and retracted, and further that other end of said expansion tube is provided with said pliable tube capable of being bent and located, said locating devices enabling said cauterizers to be located in proximity of a specific point of the body of a patient, said temperature controllers and timers intended for regulating a treatment temperature and a treatment duration of said heater.

2. The infrared rays cauterizing structure as defined in claim 1, wherein said cauterizers are composed of a heater, an infrared rays ceramic block, and a medicine plate, said heater being located at a base end of said cauterizers and formed of coil, said infrared rays ceramic block being located in a midportion of said cauterizers and provided with a plurality of through holes, said medicine plate being located at a top end of said cauterizers and formed of a predetermined drug, said heater being regulated by said temperature controllers and said timers of said base such that a treatment temperature and a treatment duration of said heater are regulated respectively by said temperature controllers and said timers, and that energy of a predetermined temperature is brought about by said ceramic block through said medicine plate.

* * * * *